US007687262B2

(12) United States Patent
Cattadoris

(10) Patent No.: US 7,687,262 B2
(45) Date of Patent: Mar. 30, 2010

(54) FLASK

(75) Inventor: Henry J. Cattadoris, Old Orchard Beach, ME (US)

(73) Assignee: Corning Incorporated, Corning, NY (US)

( * ) Notice: Subject to any disclaimer, the term of this patent is extended or adjusted under 35 U.S.C. 154(b) by 1255 days.

(21) Appl. No.: 11/187,045

(22) Filed: Jul. 22, 2005

(65) Prior Publication Data

US 2006/0019377 A1    Jan. 26, 2006

Related U.S. Application Data

(60) Provisional application No. 60/590,399, filed on Jul. 22, 2004.

(51) Int. Cl.
C12M 1/24 (2006.01)
C12M 3/00 (2006.01)

(52) U.S. Cl. .................................................. 435/304.3

(58) Field of Classification Search ............... 435/304.3
See application file for complete search history.

(56) References Cited

U.S. PATENT DOCUMENTS 5,571,721 A * 11/1996 Turner ..................... 435/305.1
6,040,493 A * 3/2000 Cooke et al. ................. 602/41
6,280,939 B1* 8/2001 Allen ............................. 435/6
7,361,310 B1* 4/2008 Mirkin et al. ............... 422/100
2002/0112814 A1* 8/2002 Hafner et al. ............ 156/272.2
2002/0178846 A1* 12/2002 Dai et al. .................... 73/866.5
2005/0011256 A1* 1/2005 Hoh ............................ 73/105

FOREIGN PATENT DOCUMENTS

EP       0 681 024       11/1995
EP       0 866 122       9/1998
JP       06-233671       8/1994

* cited by examiner

Primary Examiner—Walter D Griffin
Assistant Examiner—Lydia Edwards
(74) Attorney, Agent, or Firm—Susan S. Wilks; Thomas R. Beall

(57) ABSTRACT

The present invention provides a flask having a top piece 20 and a bottom piece 22 with optical properties on the interior surface 24 of which cells are grown. The top piece 20 and the bottom piece 22 are joined by a removable elastomeric seal 26. By disengaging the elastomeric seal 26 from the flask body 12, the top piece 20 can be separated from the bottom piece 22 providing access to the flask interior.

22 Claims, 5 Drawing Sheets

FLASK

CROSS-REFERENCE TO RELATED APPLICATIONS

This application claims the benefit of U.S. Provisional Application Ser. No. 60/590,399 filed on Jul. 22, 2004 and entitled "Flask" which is incorporated by reference herein.

BACKGROUND OF THE INVENTION

1. Field of the Invention

The present invention relates generally to the field of laboratory ware, and more particularly to flasks useful for various types of culture such as cells, tissues, and micro-organisms.

2. Technical Background

The use of culture flasks to grow or culture cells, tissues, and the like has been long practiced. A typical culture flask is made of a clear plastic structure, having a cylindrical, rectangular, or square body and a removable cap closing off a neck opening.

Harvesting of material from the flasks has traditionally been accomplished by the addition of a chemical additive, such as trypsin, to the flask in order to release the cells from the flask walls. The cells are then typically harvested from the flask through the neck opening. To facilitate removal of material from the flasks, various features have been developed including inclined ramps between the neck and growing surface and specially formed necks which allow cell scrapers to reach all the corners of the growing surface. While these features make use of the flasks somewhat more convenient, it nevertheless remains difficult to remove material from the growing surface, particularly when only selected areas are to be removed for analysis, and it is essentially impossible to remove large sections of monolayers of cells through the neck.

Various flask designs have been developed which attempt to ease gaining access to the flask interior in order to remove selected areas of the cultures or to remove large layers of cells. Some designs utilize weakened or thinner flask areas which may be broken away or more easily cut by an electric iron or other cutting tool. These arrangements have many disadvantages, the most obvious of which are the possibility of culture contamination by chips of flask material falling into the culture when the flask is cut and damage to the culture by the heat and fumes generated from melting the flask with an electric iron. Other designs have tried to avoid those disadvantages by including flask walls or sections of flask walls which are flexible, held in place by adhesive or heat sealing, and able to be peeled away from the flask body. Although minimizing the disadvantages of the previous designs, these arrangements have their own shortcomings such as possible culture contamination from contact with the adhesive, a weaker overall flask structure from lessened support from the flexible wall section, and possible puncturing of the flask body through the flexible wall section.

SUMMARY OF THE INVENTION

One aspect of the present invention relates to a flask including a top piece and a bottom piece each having a predetermined sealing surface. An elastomeric material joins the top piece and the bottom piece along some portion of both sealing surfaces to form a seal between the pieces. The top piece and the bottom piece enclose a cavity with an interior surface which is suitable for the growth of cells, tissues, and the like.

Another aspect of the present invention relates to a method of fabricating a flask seal by providing a top piece and a bottom piece each having a predetermined sealing surface in which at least one includes a track. After proper positioning of the top piece and bottom piece, an elastomeric material is melted and injected into track of the aligned top piece and bottom piece thereby forming the flask seal.

In another aspect, the present invention relates to a method of harvesting cells from a flask, such as the one described in the first aspect. Once the desired cells or layer of cells are grown on the interior surface of the flask, the seal is disengaged from the top piece and the bottom piece by stretching the elastomeric material. After the seal is removed, the top piece and bottom piece are separated and the targeted cells are collected from the interior surface of the flask.

The flasks and methods of use of the present invention result in a number of advantages over prior art flask designs and methods. For example, the design of the present invention provides a way to gain improved access to the flask interior, leaving a growth surface separated from the surrounding walls. This design enables all areas of the growth surface to be conveniently reached without special manipulation of scrapers or other tools through the flask neck. Another example is that the design of the present invention enables the skilled artisan a way of opening the flask body without the need for external tools and without generating contaminating flask particulate, debris, heat, or fumes when opened.

Additional features and advantages of the invention will be set forth in the detailed description which follows, and in part will be readily apparent to those skilled in the art from the description or recognized by practicing the invention as described in the written description and claims hereof, as well as in the appended drawing(s).

It is to be understood that both the foregoing general description and the following detailed description are merely exemplary of the invention, and are intended to provide an overview or framework for understanding the nature and character of the invention as it is claimed.

The accompanying drawings are included to provide a further understanding of the invention, and are incorporated in and constitute a part of this specification. The drawings are not necessarily to scale, and sizes of various elements may be distorted for clarity. The drawings illustrate one embodiment of the invention and together with the description serve to explain the principles and operation of the invention.

DETAILED DESCRIPTION OF THE INVENTION

Figure 1:
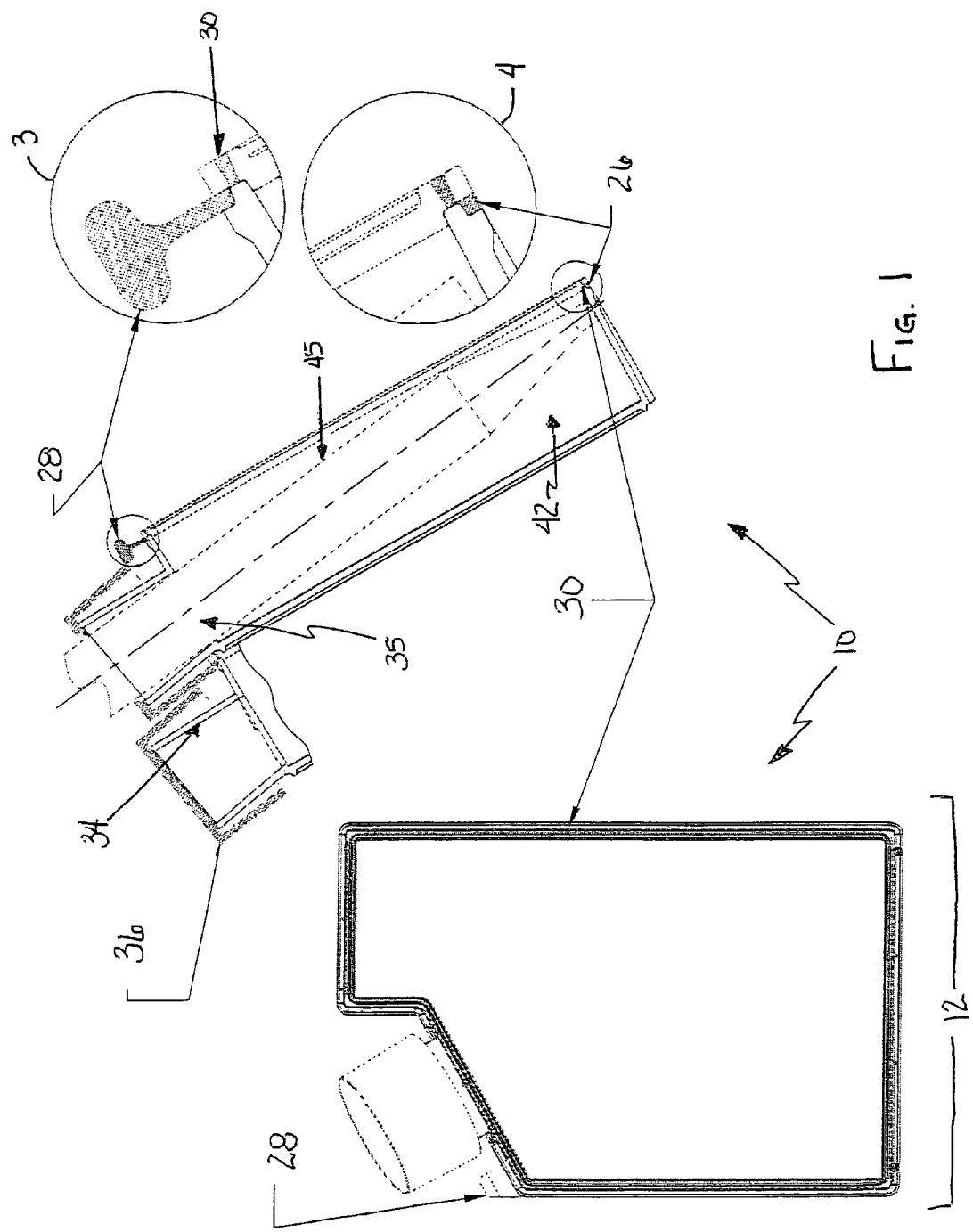
FIG. 1 is a schematic view of a flask according to one embodiment of the present invention.

One embodiment of the present invention is shown in FIG. 1. A flask 10, with a flask body 12 which includes a top piece 20 and a bottom piece 22 defining a cavity 42 with interior surfaces 24 suitable for cell, tissue, or micro-organism culture. The top piece 20 and the bottom piece 22 are joined by an elastomeric material forming a seal 26 along the sealing surfaces 33 of both pieces. Further, FIG. 1 illustrates an aperture 35, located on the flask body 12, containing a neck 34 suitable for access to the flask cavity 42 by a pipet 45. Additionally the neck 34 may be covered by a removable cap 36.

Figure 2:
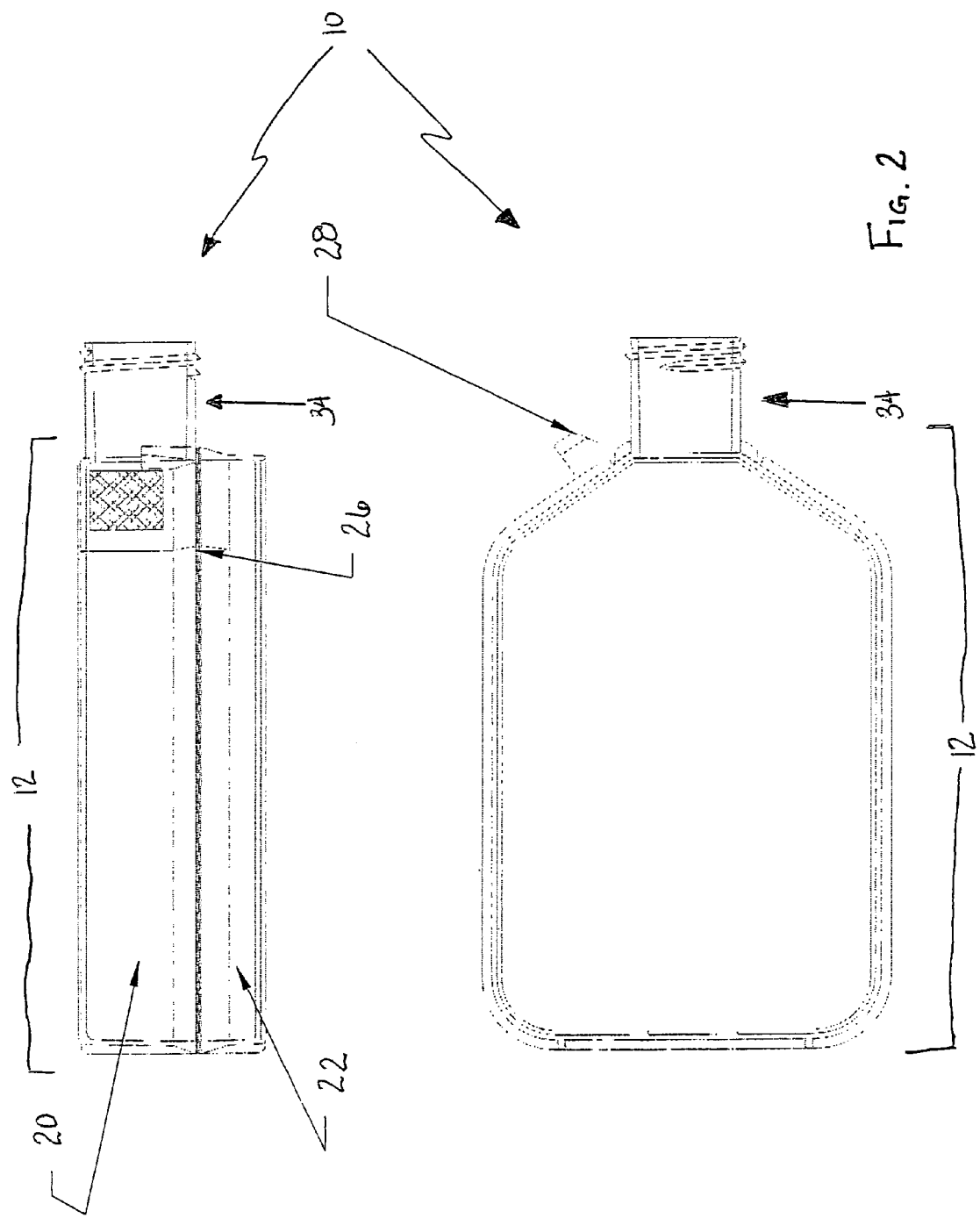
FIG. 2 is a schematic view similar to FIG. 1 showing a second embodiment of the present invention.

The flask 10 may be made by any number of acceptable manufacturing methods well known to those of skill in the art. In a preferred method, the flask is assembled from a collection of separately injection molded parts. Although any polymer suitable for molding and appropriate for the manufacture of laboratory ware may be used, polystyrene is preferred. The separately molded parts may be formed from different polymers, but are preferably the same material. Preferably the bottom piece 22 is a substantially planar, rigid, rectangular piece having a thickness sufficient to provide stability, rigidity, and optical clarity. Like the bottom piece 22, the top piece 20 is also preferably injection molded. The top piece 20 preferably is molded such that the at least one wall 21 and the neck 34 for the removable cap 36 are molded together integrally, forming a rectangular shape. It should be noted that the rectangular shape of the top piece 20 and bottom piece 22 and the planar aspect of the bottom piece 22 are not necessary for the present invention. Other embodiments of the top piece 20 and bottom piece 22 may have a variety of shapes, examples of which include concave, convex, circular, square, parallelogram, triangular, trapezoidal, and polygonal. Further, there are a variety of cap 36 and neck 34 arrangements which may be used for this invention besides the conventional cap 36 and neck 34 arrangement, illustrated in FIG. 2, which extends beyond the flask body 12 perimeter. One example of an unconventional flask embodiment is illustrated in FIG. 1 and described in U.S. patent application Ser. No. 10/750,474, which is hereby incorporated herein by reference as though fully set forth in its entirety, for a more detailed explanation of a flask shape and recessed cap 36 and neck 34 arrangement. Additionally, another example of a flask embodiment provides access to the interior of the flask directly through the flask body 12 through an aperture that is made impermeable to liquid by means of a septum. Hence, the flask shape, cap and neck arrangement, or any additional distinguishing features, such as a septum or respirator within the flask body, may vary greatly depending upon the needs of those skilled in the art of cell, tissue, or micro-organism culturing.

Preferably the interior surface 24 of the bottom piece 22 is treated to make it hydrophilic in order to enhance cell attachment and growth. Any number of methods known in the art may be used to treat the interior surface, including, for example, plasma discharge, corona discharge, gas plasma discharge, ion bombardment, ionizing radiation, and high intensity UV light. Although cell attachment is typically targeted for only one surface, in particular the interior surface 24 of the bottom piece 22, other parts of the flask may be treated so as to enable cell growth on all surfaces of the flask interior.

Figure 3:
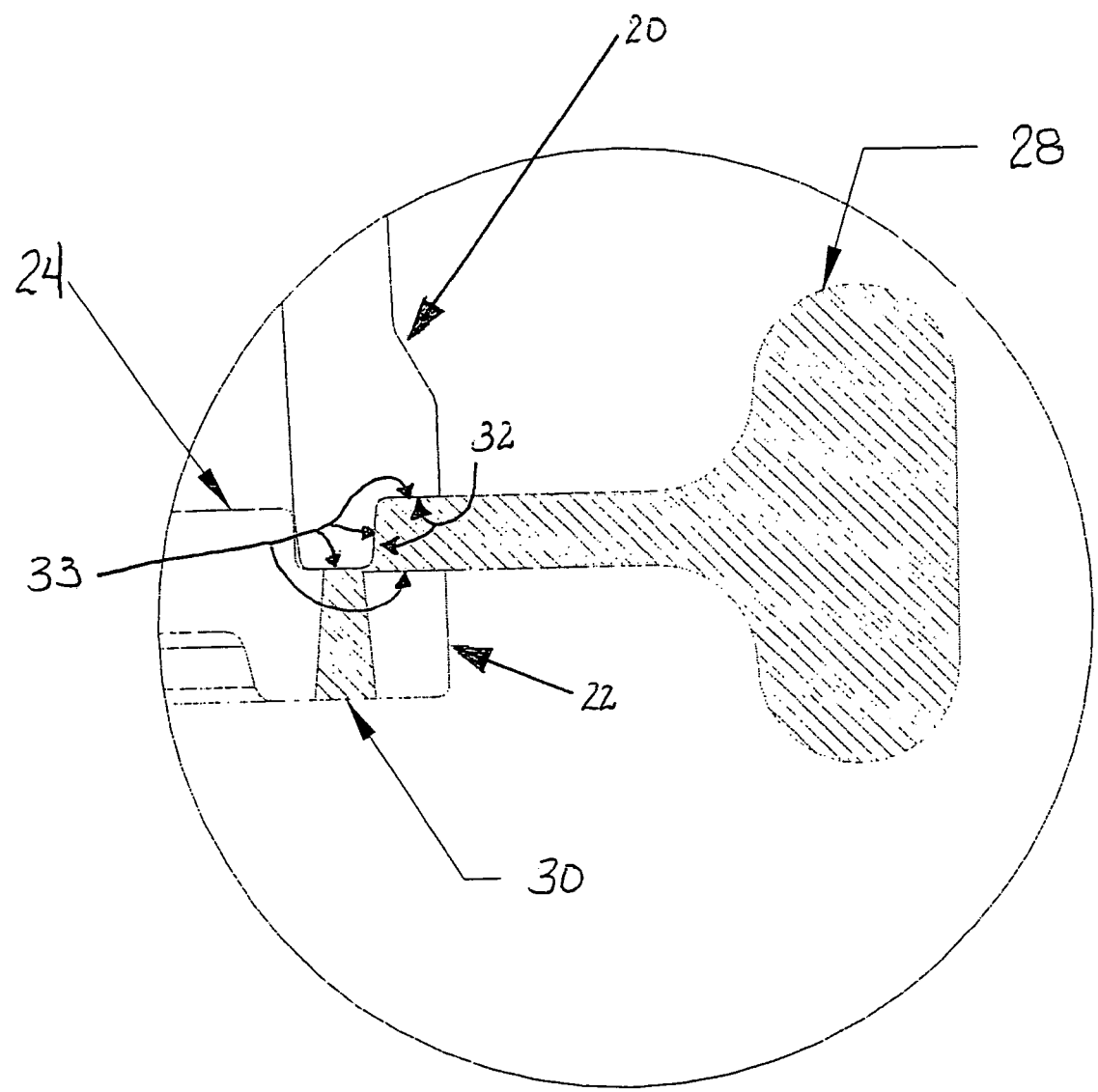
FIG. 3 is a cross-sectional view of part of a flask, according to 3 in FIG. 1.
Figure 4:
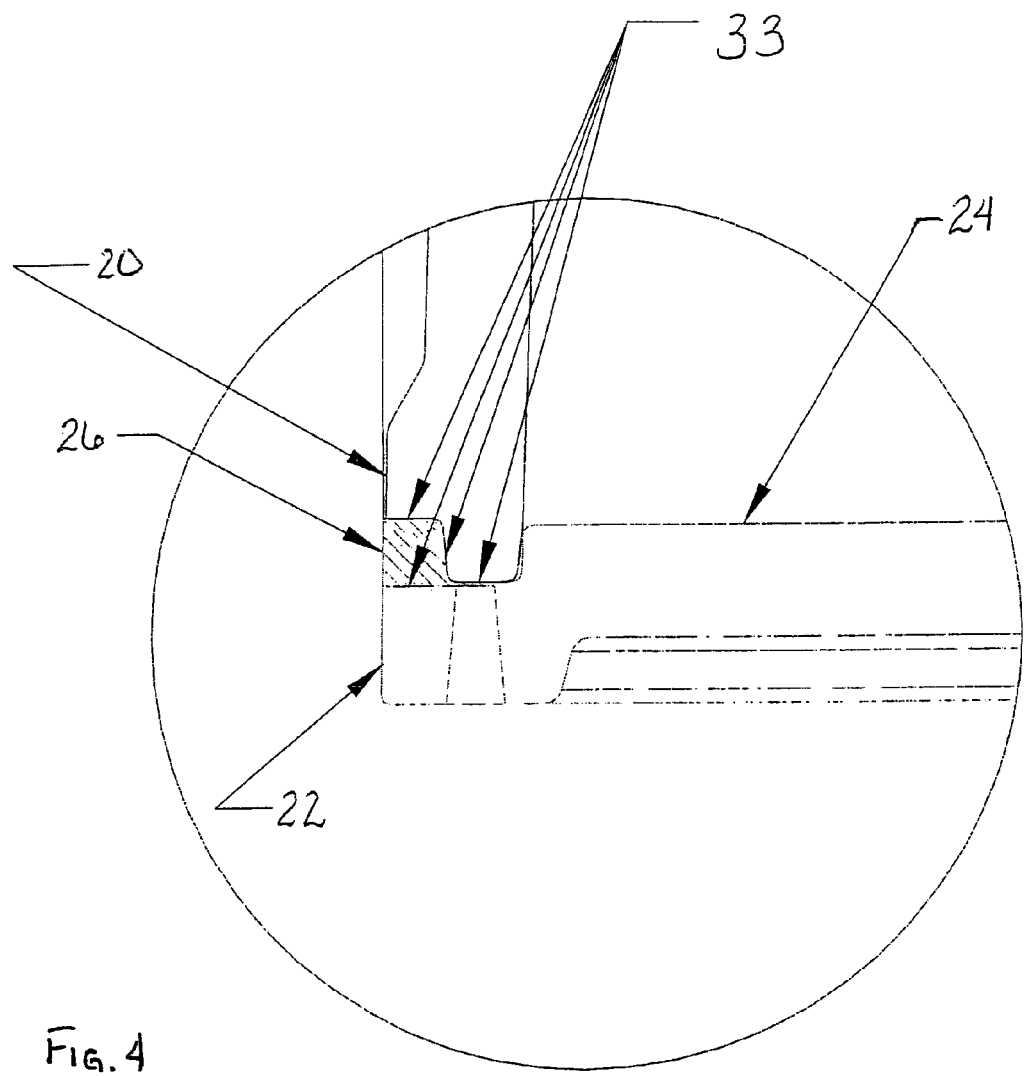
FIG. 4 is a cross-sectional view of part of a flask, according to 4 in FIG. 1.

A seal 26 is formed from an elastomeric material, joining the top piece 20 and the bottom piece 22. While there are a wide variety of elastomeric materials that may be used for the seal 26, such as a silicone elastomeric material or thermoplastic elastomers, a thermoplastic olefin elastomer is more preferred. One aspect of the present invention relates to a method of forming the seal 26. First the top piece 20 and the bottom piece 22 are molded, including a track 32 in at least one of the sealing surfaces 33. Then the newly molded top piece 20 and bottom piece 22 are positioned in a mold to bring the sealing surfaces 33 into proper alignment. Once properly aligned, the top piece 20 and the bottom piece 22 enclose the cavity 42 with interior surfaces 24 suitable for cell, tissue, or micro-organism culture. Additionally, proper alignment of the top piece 20 and the bottom piece 22 properly positions the track 32 of the sealing surface 33 to receive the seal 26, as illustrated in FIGS. 3 and 4. Finally, the elastomeric material is melted and injected into the mold holding the aligned top piece 20 and bottom piece 22 and filling the track 32 of the sealing surface 33. The elastomeric material partially melts the sealing surfaces 33, bonds to the top piece 20 and the bottom piece 22, and forms a hermetic seal 26. It should be noted that a preferred embodiment of the present invention, as seen in FIGS. 3 and 4, includes that the top piece 20 and the bottom piece 22 are positioned together in such a way that when the melted elastomeric material is added there is no contact between the elastomeric material and the interior surfaces 24 of the flask. This aspect helps ensure that the elastomeric material will not contaminate nor interact with the cell culture. Additionally, FIG. 3 illustrates a preferred embodiment in which the seal 26 includes a series of elastomeric retention structures 30 molded into the bottom piece 22, while FIG. 4 illustrated another embodiment without the retention structures 30. When included, the retention structures 30 provide greater stability for the seal 26 by increasing the amount of surface area available for attachment. Additionally, FIG. 3 further illustrates a preferred embodiment in which the seal 26 includes an elastomeric tab 28 for easier gripping of the seal 26 when ready to remove it from the flask body 12. Those skilled in the art will agree that there is a variety of ways of making a flask seal and various modifications or variations can be made without departing from the spirit and scope of the present invention.

Figure 5:
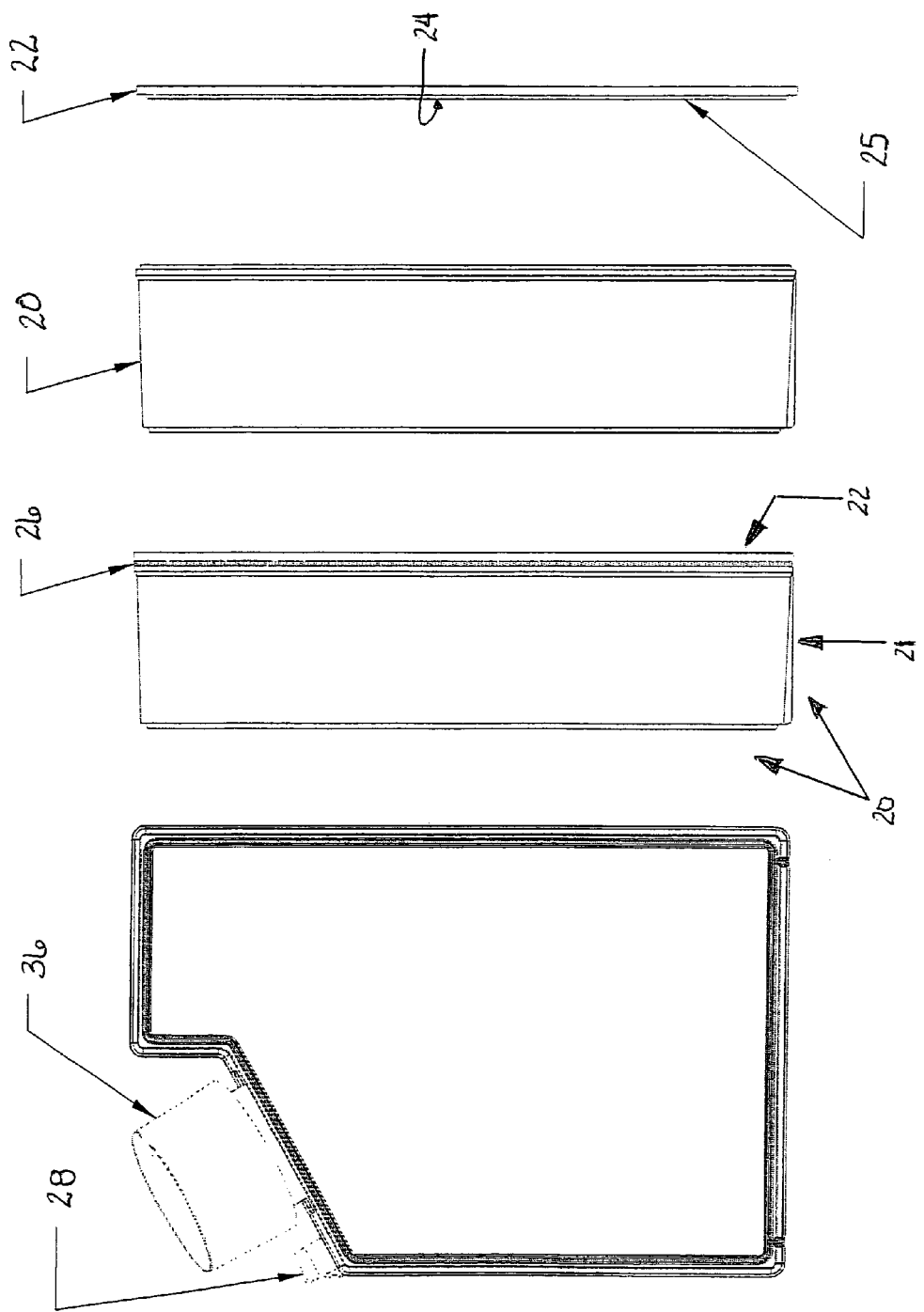
FIG. 5 is an exploded view of a flask according to the embodiment of FIG. 1.

In use, the flask of the current invention is employed according to accepted cell growth methods. Once the cells are ready for harvesting, the present invention provides a method of opening the flask body 12 to gain complete access to the flask interior surfaces 24. First, once a desired cell growth is achieved on the growth region 25 of the interior surface 24, the seal 26 can be disengaged from the top piece 20 and the bottom piece 22 by stretching the elastomeric material, preferably by gripping and pulling the provided tab 28. Stretching the elastomeric material will cause it to shrink and pull away from the sealing surfaces 33 of the top piece 20 and bottom piece 22. In certain embodiments, in which the retention structures 30 are used, the stretching of the elastomeric material will additionally shear off the retention structures 30, thus leaving them embedded within the bottom piece 22. Once the seal 26 is broken, the top piece 20 and the bottom piece 22 may easily be separated, as illustrated in FIG. 5, thereby leaving the preferred flat bottom piece 22 fully accessible for cell or tissue harvesting.

From the foregoing description, the advantages of the present invention over the prior art will be fully appreciated. The present invention provides very easy access to the full flask interior surface 24 when the elastomeric seal 26 is broken and the top piece 20 and bottom piece 22 are separated. In presently available prior art flasks, the only access to the growing surface is to cut the flask open or to peel-off a flexible section of the flask wall. As previously described each of these designs has their own disadvantages which are improved upon by the present invention.

It will be apparent to those skilled in the art that various modifications and variations can be made to the present invention without departing from the spirit or scope of the invention. Thus, it is intended that the present invention cover the modifications and variations of this invention provided they come within the scope of the appended claims and their equivalents.

What is claimed is:

1. A flask comprising:
   a top piece having a predetermined sealing surface; and a bottom piece having a predetermined sealing surface, wherein the top piece and the bottom piece are joined by an elastomeric material along some portion of the sealing surface of the top piece and some portion of the sealing surface of the bottom piece, the elastomeric material forming a seal between the top piece and the bottom piece, the top piece and the bottom piece enclosing a cavity;

wherein the elastomeric material forms a grippable tab, whereby said tab, once pulled, is structured and arranged to stretch the elastomeric material and release the seal between the top piece and the bottom piece.

2. The flask according to claim 1 wherein the top piece and the bottom piece each have a shape individually selected from the group consisting of planar, concave, convex, rectangular, circular, square, parallelogram, triangular, trapezoidal, and polygonal.

3. The flask according to claim 1 wherein the top piece comprises at least one wall extending toward the bottom piece.

4. The flask according to claim 1 wherein the flask further comprises at least one aperture providing access to the cavity.

5. The flask according to claim 4 wherein the at least one aperture is a neck extending from the flask; said neck adapted to receive a removable cap.

6. The flask according to claim 1 wherein the flask further comprises an interior surface suitable for cell, tissue, or micro-organism culture.

7. The flask according to claim 6 wherein the bottom piece comprises a substantially planar growth region on said interior surface.

8. The flask according to claim 1, wherein the elastomeric material is a thermoplastic elastomer.

9. The flask according to claim 1, wherein the elastomeric material is a thermoplastic olefin elastomer.

10. The flask according to claim 1 wherein the seal is hermetic.

11. The flask according to claim 1 wherein the seal is reinforced by a series of elastomeric retention structures embedded in said bottom piece.

12. The flask according to claim 6 wherein the top piece and bottom piece are positioned such that the seal is not in contact with the interior surfaces.

13. The flask according to claim 1 wherein the elastomeric material is capable of being stretched to disengage the seal from the top piece and the bottom piece.

14. A method for fabricating a flask seal, the method comprising:
   providing a top piece and a bottom piece, each having a predetermined sealing surface, wherein at least one sealing surface includes a track;
   positioning the top piece and the bottom piece together;
   melting an elastomeric material; and
   injecting the melted elastomeric material into the track of the joined top piece and bottom piece to form a seal enclosing a flask body; and
   forming a grippable tab from the melted elastomeric material wherein the grippable tab extends from the track.

15. The method for fabricating a flask seal according to claim 14 comprising the top piece and the bottom piece each having a shape individually selected from the group consisting of planar, concave, convex, rectangular, circular, square, parallelogram, triangular, trapezoidal, and polygonal.

16. The method for fabricating a flask seal according to claim 14 wherein the elastomeric material is a thermoplastic elastomer.

17. The method for fabricating a flask seal according to claim 14 wherein the elastomeric material is a thermoplastic olefin elastomer.

18. The method for fabricating a flask seal according to claim 14 wherein the seal is hermetic.

19. The method for fabricating a flask seal according to claim 14 wherein the flask body comprises an interior surface suitable for cell, tissue, or micro-organism culture.

20. The method for fabricating a flask seal according to claim 19 wherein the top piece and bottom piece are positioned such that the seal is not in contact with the interior surface.

21. The method for fabricating a flask seal according to claim 14 wherein said elastomeric material is reinforced by a series of elastomeric retention structures embedded in said flask body.

22. A method for harvesting cells from a flask, the method comprising:
   providing the flask of claim 1;
   growing a layer of cells within said flask;
   disengaging the seal from the top piece and the bottom piece by pulling on the tab and stretching the elastomeric material;
   separating the top piece and the bottom piece; and
   collecting cells from within said flask.

* * * * *